United States Patent [19]

Dutta et al.

[11] Patent Number: 5,122,308
[45] Date of Patent: * Jun. 16, 1992

[54] PROCESS FOR THE OXIDATION OF ALCOHOLS TO ACIDS

[75] Inventors: Tamal K. Dutta; Lynn H. Slaugh, both of Houston, Tex.

[73] Assignee: Shell Oil Company, Houston, Tex.

[*] Notice: The portion of the term of this patent subsequent to Jun. 16, 2009 has been disclaimed.

[21] Appl. No.: 552,392

[22] Filed: Jul. 13, 1990

[51] Int. Cl.⁵ .................................................. C09F 7/02
[52] U.S. Cl. ................................ 554/135; 562/512.2; 562/538; 562/540; 554/136; 554/207
[58] Field of Search ............... 260/413, 406, 410.9 R; 562/538, 512.8, 540; 560/239

[56] References Cited

U.S. PATENT DOCUMENTS

| | | | |
|---|---|---|---|
| 3,818,060 | 6/1974 | Forster et al. | 260/413 |
| 3,997,578 | 12/1976 | Sheng | 260/413 |
| 4,015,060 | 3/1977 | Karayannis et al. | 526/141 |
| 4,096,196 | 6/1978 | Boudakian | 260/650 F |
| 4,207,310 | 6/1980 | Langford | 424/150 |
| 4,225,694 | 9/1980 | Dalton et al. | 562/506 |
| 4,996,007 | 2/1991 | Caro et al. | 562/538 |

Primary Examiner—Jose G. Dees
Assistant Examiner—Deborah D. Carr
Attorney, Agent, or Firm—Pamela J. McCollough

[57] ABSTRACT

The instant invention relates to a process for the oxidation of primary alcohols to the corresponding acids, which comprises contacting and thereby reacting an alcohol with a tertiary amine oxide compound at elevated temperatures in the presence of a homogeneous oxidation catalyst comprising a Group VIII metal and a promoter comprising a quaternary ammonium bromide, and subsequently separating out acids from the reaction mixture product.

15 Claims, No Drawings

PROCESS FOR THE OXIDATION OF ALCOHOLS TO ACIDS

FIELD OF THE INVENTION

This invention relates to an improved process for the oxidation of alcohols to acids using a tertiary amine oxide oxygen activator in the presence of a homogeneous oxidation catalyst and a promoter.

BACKGROUND OF THE INVENTION

Alcohols, particularly primary alcohols, are readily available in large commercial quantities. Processes to convert primary alcohols to acids fill a useful need in the industrial world. Acids have been used commercially for the manufacture of synthetic lubricants and soaps.

In the past, various processes have been developed for the production of acids. It has been proposed to treat various alcohols with an oxidizing agent in the presence of a catalyst, such as ruthenium and a solvent to produce the corresponding acids. Such processes, however, have generally produced high yields of aldehydes and rather low yields of acids. Since processes that produce high yields of acids are particularly desired, it is an object of this invention to provide a process for the conversion of alcohols to the corresponding carboxylic acids having a high selectivity to acids.

It has been found that high selectivity to acids can be achieved by a process for oxidizing alcohols to acids which comprises reacting an alcohol with a tertiary amine oxide oxidant at elevated temperatures in the presence of an oxidation catalyst comprising a Group VIII metal and a promoter comprising a quaternary ammonium bromide and thereafter separating out the acids formed from the reaction product mixture.

SUMMARY OF THE INVENTION

The instant invention relates to an improved process for the oxidation of primary alcohols to acids, which comprises contacting and thereby reacting at elevated temperatures an alcohol with a tertiary amine oxide compounds in the presence of an oxidation catalyst comprising a Group VIII metal and a promoter comprising a quaternary ammonium bromide, and subsequently separating out acids from the reaction mixture product.

DETAILED DESCRIPTION OF THE INVENTION

The instant process comprises reacting a primary alcohol with a tertiary amine oxide oxidant at elevated temperatures in the presence of an oxidation catalyst comprising a Group VIII metal and a promoter comprising a quaternary ammonium bromide.

Alcohols typically used in the process of the present invention are primary mono-hydric aliphatic alcohols. The aliphatic alcohols preferably have from one to about 30 carbon atoms, with $C_6$ to $C_{24}$ alcohols considered more preferred and $C_8$ to $C_{20}$ alcohols considered most preferred. As a general rule, the aliphatic alcohols are primarily of straight-chain structure. Specific examples of primary straight-chain monohydric aliphatic alcohols include ethanol, hexanol, octanol, dodecanol, pentadecanol and octadecanol.

Mixtures of alcohols are also suitable for purposes of this invention. Mixtures of higher (e.g., $C_8$ to $C_{20}$) monohydric aliphatic alcohols are known to be commercially prepared, for instance, by hydroformylation of olefins or by reduction of naturally occurring fatty esters. Specific examples of commercially available alkanol mixtures in the $C_9$ to $C_{18}$ range are the NEODOL detergent alcohols, trademark of and manufactured by Shell Chemical Company. e.g., the products identified as NEODOL 91 alcohols (predominantly in the $C_9$ to $C_{11}$ range), NEODOL 23 alcohols (predominantly in the $C_{12}$ to $C_{13}$ range), NEODOL 25 alcohols (predominantly in the $C_{12}$ to $C_{15}$ range) and NEODOL 45 alcohols (predominantly in the $C_{14}$ to $C_{15}$ range)

The oxidant in the process of the instant invention is a tertiary amine oxide compound. The tertiary amine oxide oxidant reacts with a primary alcohol at temperatures in the range of from about 40° C. to about 200° C. and converts it to primarily acids, although some aldehydes and esters are also formed. The process of the instant invention can also be carried out in the presence of an additional oxidant such as oxygen or air, or in an inert atmosphere.

The tertiary amine oxides suitable for use in the process of the instant invention are those having the general formula:

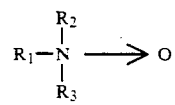

wherein $R_1$ and $R_2$ are alkyl groups, preferably methyl groups or ethyl groups, which are the same or different, and $R_3$ is a phenyl group or alkyl substituted phenyl group, a benzyl group or an alkyl substituted benzyl group, a cyclohexyl group or an alkyl substituted cyclohexyl group, a cyclohexanemethyl group or an alkyl substituted cyclohexanemethyl group; or wherein $R_1$ is an alkyl group, preferably a methyl group or an ethyl group, and N, $R_2$ and $R_3$ together form part of a saturated or unsaturated heterocyclic group, or where N, $R_1$, $R_2$ and $R_3$ together form part of a saturated or unsaturated heterocyclic group or bridged heterocyclic group.

When N, $R_2$ and $R_3$, or N, $R_1$, $R_2$ and $R_3$ form a heterocyclic or bridged heterocyclic group, a second tertiary amine oxide group can also optionally be included in the heterocyclic or bridged heterocyclic group.

Examples of suitable tertiary amine oxides include: N,N-dimethyl benzylamine oxide; N,N-diethyl benzylamine oxide; N-methyl N-ethyl benzylamine oxide; pyridine N-oxide; α-picoline N-oxide; β-picoline N-oxide; γ-picoline N-oxide; pyrazine N-oxide; pyrazine N,N'-dioxide; N-methyl piperidine N-oxide; N-ethyl piperidine N-oxide; N-methyl piperazine N-oxide; N,N'-dimethyl piperazine N,N'-dioxide; triethylenediamine N-oxide; triethylenediamine N,N'-dioxide; N-methylmorpholine N-oxide; N-ethyl morpholine N-oxide; quinoline N-oxide; N-methyl pyrrole N-oxide; N-methyl pyrrolidine N-oxide; N,N-dimethyl cyclohexylamine N-oxide; N, N-dimethyl cylcohexanemethylamine N-oxide; and N,N-dimethylaniline N-oxide. In a preferred embodiment, the tertiary amine oxide oxidant is N-methylmorpholine N-oxide.

The tertiary amine oxide oxidant should be present in an amount sufficient to obtain complete oxidation of the alcohol to an acid. Typically, the tertiary amine oxide is used in an amount sufficient to supply between about 0.4 and about 1.8 mole equivalents of oxygen per mole of alcohol.

The tertiary amine oxide may be utilized in a one-phase hydrocarbon system or in a two-phase hydrocarbon/water system. The solubility of the tertiary amine oxide in the aqueous phase will depend on the presence of water solubilizing substituents on the tertiary amine oxide, such as, for example, alkylsulfonates, arylsulfonates and the like. The use of a two phase system can have certain processing advantages, particularly when the tertiary amine oxide is more soluble in the aqueous phase than in the hydrocarbon phase and the alcohol and the product acids, aldehydes and esters are more soluble in the hydrocarbon phase than in the aqueous phase. In the latter case, the organic phase contains unreacted alcohol and the major portion of the product acids, aldehydes and esters and the aqueous phase contains the tertiary amine oxide and a residual amount of product acids, aldehydes and esters, which will allow a ready separation of product acids, aldehydes and esters and reactant alcohols from the oxygen activator. Long chain alcohols are suitably processed with this two phase system.

In addition to the use of water as a solvent as indicated above, other organic solvents can be utilized, such as alkanes, aromatics, such as benzene, toluene and xylene; alkanes, halo-substituted aromatics, amides, amines, ethers, sulfoxides, ketones, etc.. Solvents selected should not react with either the reactant alcohol or the product acids.

The catalyst utilized in accordance with the present invention is homogeneous oxidation catalyst comprising a Group VIII metal. With the catalyst being homogeneous, it is preferred that a two phase hydrocarbon/water system be utilized and that the catalyst be soluble in the aqueous phase in order to facilitate separation of the catalyst from the product acids, aldehydes and esters. Preferably, the Group VIII metal is selected from the group consisting of ruthenium, rhodium, platinum, palladium and mixtures thereof. In a particularly preferred embodiment, the Group VIII metal is ruthenium. The amount of catalyst utilized in the present process is generally in amounts the range of from about 0.1 percent by weight to about 15 percent by weight, basis substrate alcohol and preferably, from about 1 percent by weight to about 8 percent by weight.

The process of the instant invention is also carried out in the presence of a promoter. A promoter comprising a quaternary ammonium bromide is utilized. Preferably, the promoter is quaternary alkylammonium bromide wherein the alkyl moieties have carbon numbers ranging from 1 to about 20. Higher alkylammonium bromides are preferred. Suitable quaternary alkylammonium bromides include didecyldimethylammonium bromide, tetrapropylammonium bromide, cetyldimethylethylammonium bromide and cetyltrimethylammonium bromide, with didecyldimethylammonium bromide being preferred. The promoter is typically used in amounts ranging between about 1 percent by weight and about 100 percent by weight, basis substrate alcohol, preferably, between about 10 percent by weight and about 80 percent by weight, and more preferably, between about 50 percent by weight and about 60 percent by weight.

The alcohol oxidation reaction may be carried out in a batch reactor or in a continuous flow reactor. For example, the alcohol and the tertiary amine oxide oxidant may be trickled over a bed of inert support materials, such as alumina raschig rings or berl saddles, in the presence of air or nitrogen and in the presence of the homogeneous catalyst. Other continuous reactor configurations will be readily apparent to one skilled in the art.

Batch reactors, such as autoclaves, are also suitable. For example, the primary alcohol, an aqueous solution of the tertiary amine oxide and the homogeneous oxidation catalyst can be loaded into an autoclave, the autoclave sealed and charged with an oxygen-containing gas, heated to a desired reaction temperature and the reaction allowed to proceed.

The process in the instant invention is carried out at elevated temperatures. The reaction temperature is typically in the range of from about 40° C. to 200° C., preferably from about 50° C. to about 100° C. and more preferably, from about 55° C. to about 65° C. While the reaction will proceed at lower temperatures, temperatures greater than about 40° C, preferably greater than about 50° C., are necessary in order to obtain a high selectivity to acids. Reaction pressures for the instant process are not critical and will typically range from about atmospheric to about 150 atmospheres, preferably from about 35 atmospheres to about 100 atmospheres although higher and lower pressures can be utilized.

For the two-phase system, after reaction there will be a hydrocarbon phase containing unreacted alcohol and the major portion of the product acids, aldehydes and esters. The hydrocarbon phase may be diluted with an inert organic solvent, such as an alkane. There will also be an aqueous phase containing the oxidized tertiary amine oxide, promoter, a small amount of alcohol and product acids, aldehydes and esters, and the homogeneous oxidation catalyst. The hydrocarbon phase is processed, for example, by distillation, to recover the product acids, aldehydes and esters. The product acids, aldehydes and esters may then be distilled to recover the product acids. The aqueous phase may also be processed to remove any residual alcohol or acids/aldehydes/esters, say by liquid-liquid extraction with an organic solvent.

For the single phase hydrocarbon system, after reaction, the hydrocarbon phase is processed by conventional techniques such as distillation, liquid-liquid extraction with water, filtration, etc; in order to separate the product acids, aldehydes and esters, the oxidized tertiary amine oxide, unreacted alcohol and any oxidation catalyst and promoter.

The ranges and limitations provided in the instant specification and claims are those which are believed to particularly point out and distinctly claim the instant invention. It is, however, understood that other ranges and limitations that perform substantially the same function in substantially the same way to obtain the same or substantially the same result are intended to be within the scope of the instant invention as defined by the instant specification and claims.

The invention will be described by the following examples which are provided for illustrative purposes and are not to be construed as limiting the invention.

EXPERIMENTAL PROCEDURE

In a typical experiment a round bottom flask (50 ml capacity), equipped with a stir bar and a nitrogen (1 atmosphere) line capping the neck, was charged in a dry box (pre-purified nitrogen-gas purged) with 10.0 grams of solvent (for example, acetone); 1.56 grams (8.37 mmols) of alcohol substrate (for example, 1-dodecanol);

0.50 grams of dodecane; 0.98 grams (8.37 mmols) of tertiary amine oxide (for example, N-methyl morpholine-N-oxide); and 0.13 grams of $RuCl_3 \times H_2O$ catalyst. In the experiments containing a promoter, 0.94 grams (2 mmols) of quaternary ammonium bromide (for example, didecyldimethylammonium bromide) was added.

The round bottom flask was then removed from the dry box and magnetically stirred and charged with a continuous flow of 1 atmosphere of nitrogen. The flask was then heated to 65° C. (internal temperature) while maintaining rapid mechanical for a period of about 2 hours until no further pressure drop occurred. The hot flask was then allowed to cool down to room temperature.

The solution of the crude reaction product mixture was filtered through glass wool and then analyzed by gas liquid chromatography (GLC) using a Hewlett-Packard 5890A gas chromatograph fitted with a hydrogen flame ionization detector and a data processor. The peaks of the chromatograms were identified qualitatively by comparison of their retention times with those of standards and by GC/MS technique. The quantitative estimation of the percent composition of the reaction mixture was obtained from the integration of the areas of the peaks in the chromatograms.

ILLUSTRATIVE EMBODIMENT I

Following the experimental procedure described above experiments were carried out in the presence and the absence of a promoter. The experimental conditions and the results are shown in Table 1 below.

TABLE 1

| | Oxidation of Alcohol:Effect of Promoter | | | | |
|---|---|---|---|---|---|
| | Pro- | Conver- | Selectivity, % | | |
| Substrate | moter | sion, % | $C_{12}$-Acid | $_{12}$-Aldehyde | $C_{24}$-Ester |
| 1-Do-decanol | DDAB | 51.88 | 57.72 | 19.0 | 0.0 |
| 1-Do-decanol | None | 31.65 | 0.0 | 100.0 | 0.0 |
| Conditions | | | | | |
| Solvent | Acetone, 10.0 grams | | | | |
| Promoter | DDAB is Didecyldimethylammonium bromide, 0.94 g (2 mmols) | | | | |
| Catalyst | $RuCl_3 \times H_2O$, 0.13 g (0.63 mmols) | | | | |
| Oxidant | N-methylmorpholine-N-oxide (0.98 g, 8.37 mmols) | | | | |
| Oxidation Temp. | 65° C. | | | | |
| Oxidation Reaction Time | 2 hrs. | | | | |

What is claimed is:

1. A process for the oxidation of primary alcohols to the corresponding acids, which comprises contacting and thereby reacting an alcohol with a tertiary amine oxide compound at elevated temperatures in the presence of a homogeneous oxidation catalyst comprising a Group VIII metal and a promoter comprising a quaternary ammonium bromide, and subsequently separating out acids from the reaction mixture product.

2. The process of claim 1 wherein the oxidation is carried out at a temperature ranging from about 40° C. to about 200° C.

3. The process of claim 2 wherein the oxidation is carried out at a temperature ranging from about 50° C. to about 100° C.

4. The process of claim 1 wherein said alcohol is a primary mono-hydric aliphatic alcohols.

5. The process of claim 4 wherein said alcohol contains from one to about 30 carbon atoms.

6. The process of claim 5 wherein said alcohol contains from about 8 about 20 carbon atoms.

7. The process of claim 1 wherein said Group VIII metal is selected from the group consisting of ruthenium, rhodium, platinum, palladium and mixtures thereof.

8. The process of claim 7 wherein said Group VIII metal is ruthenium.

9. The process of claim 8 wherein said catalyst is ruthenium chloride.

10. The process of claim 1 wherein the promoter is a quaternary alkylammonium bromide.

11. The process of claim 10 wherein the quaternary alkyl ammonium bromide is didecyldimethylammonium bromide.

12. The process of claim wherein the tertiary amine oxide compound is N-methylmorpholine N-oxide.

13. A process for the oxidation of primary alcohols to the corresponding acids, which comprises contacting and thereby reacting an alcohol with a tertiary amine oxide compound at a temperature in the range of from about 50° C. to about 100° C. in the presence of a homogeneous oxidation catalyst comprising ruthenium and a promoter comprising a quaternary alkylammonium bromide, and subsequently separating out acids from the reaction mixture product.

14. The process of claim 13 wherein the quaternary alkylammonium bromide is didecyldimethylammonium bromide.

15. The process of claim 13 wherein the tertiary amine oxide compound is N-methylmorpholine N-oxide.

* * * * *